United States Patent [19]

Effland et al.

[11] Patent Number: 5,631,270
[45] Date of Patent: May 20, 1997

[54] SUBSTITUTED PYRIDINYLAMINO-1H-INDOLES, 1H-INDAZOLES, 2H-INDAZOLES, BENZO [B]THIOPHENES AND 1,2-BENZISOTHIAZOLES

[75] Inventors: Richard C. Effland; Joseph T. Klein, both of Bridgewater; Lawrence L. Martin, Lebanon, all of N.J.

[73] Assignee: Hoechst Marion Roussel, Inc., Cincinnati, Ohio

[21] Appl. No.: 464,994

[22] Filed: Jun. 5, 1995

Related U.S. Application Data

[62] Division of Ser. No. 38,427, Mar. 25, 1993, Pat. No. 5,424,322, which is a division of Ser. No. 925,822, Aug. 7, 1992, Pat. No. 5,246,947, which is a division of Ser. No. 764,031, Sep. 23, 1991, Pat. No. 5,185,350.

[51] Int. Cl.⁶ .................. A61K 31/44; A61K 31/38; A61K 31/405; A61K 31/415
[52] U.S. Cl. .................. 514/337; 514/338; 514/339
[58] Field of Search ................ 514/338, 339, 514/337; 546/270, 271, 273, 274

[56] References Cited

U.S. PATENT DOCUMENTS

| | | | |
|---|---|---|---|
| 4,970,219 | 11/1990 | Effland et al. | 514/339 |
| 5,006,537 | 4/1991 | Efflaud et al. | 514/339 |

*Primary Examiner*—Phyllis G. Spivack
*Attorney, Agent, or Firm*—J. Michael Dixon

[57] ABSTRACT

This invention relates to substituted pyridinylamino-1H-indoles, 1H-indazoles, 2H-indazoles, benzo[b]thiophenes and 1,2-benzisothiazoles of the formula

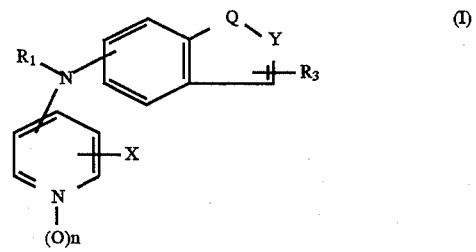

wherein Q is S, N or $NR_2$;
Y is CH, N or $NR_2$;
$R_1$ is hydrogen, loweralkyl, loweralkynyl, loweralkenyl, arylloweralkyl, loweralkoxycarbonylaminoloweralkylcarbonyl, arylloweralkoxycarbonylaminoloweralkylcarbonyl, aminoloweralkylcarbonyl, loweralkoxycarbonyl or acyl;
$R_2$ is hydrogen or loweralkyl;
$R_3$ is hydrogen or loweralkyl;
X is hydrogen, loweralkyl, halogen; and
n is 0 or 1;

or a pharmaceutically acceptable acid addition salt thereof that are useful in the treatment of memory dysfunctions.

1 Claim, No Drawings

SUBSTITUTED PYRIDINYLAMINO-1H-INDOLES, 1H-INDAZOLES, 2H-INDAZOLES, BENZO [B]THIOPHENES AND 1,2-BENZISOTHIAZOLES

This is a division of application Ser. No. 038,427, filed Mar. 25, 1993, now U.S. Pat. No. 5,424,322, which is a divisional application of prior application Ser. No. 925,822, filed Aug. 7, 1992, now U.S. Pat. No. 5,246,947, which is a divisional application of prior application Serial No. 764,031, filed Sep. 23, 1991, now U.S. Pat. No. 5,185,350.

This invention relates to substituted pyridinylamino-1H-indoles, 1H-indazoles, 2H-indazoles, benzo[b]thiophenes and 1,2-benzisothiazoles of the formula

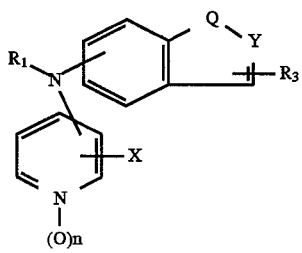

(I)

wherein

Q is S, N or $NR_2$;

Y is CH, N or $NR_2$;

$R_1$ is hydrogen, loweralkyl, loweralkynyl, loweralkenyl, aryl loweralkyl, loweralkoxycarbonylaminoloweralkylcarbonyl, arylloweralkoxycarbonylaminoloweralkylcarbonyl, aminoloweralkylcarbonyl, loweralkoxycarbonyl or acyl;

$R_2$ is hydrogen or loweralkyl;

$R_3$ is hydrogen or loweralkyl;

X is hydrogen, loweralkyl or halogen; and n is 0 or 1; or a pharmaceutically acceptable acid addition salt thereof.

The compounds of this invention are useful in the treatment of memory dysfunctions characterized by a cholinergic deficit such as the type associated with Alzheimer's disease and other memory disorders.

Compounds of this invention also have utility as modulators of neurotransmitter function such as noradrenergic and serotonergic and as such are useful for the treatment of depression and personality disorders such as obsessive compulsive disorders.

Additionally, compounds of this invention are useful as topical antiinflammatory agents for the treatment of various dermatoses.

Unless otherwise stated or indicated, the following definitions shall apply throughout the specification and the appended claims.

The term loweralkyl shall mean a straight or branched alkyl group having from 1 to 6 carbon atoms. e.g., methyl, ethyl, n-propyl, isopropyl. n-butyl, isobutyl, sec-butyl, t-butyl and straight and branched-chain pentyl and hexyl.

The term halogen shall mean fluorine, chlorine, bromine or iodine.

The term aryl shall mean a phenyl group substituted with 0, 1 or 2 substituents each of which being independently lower alkyl, loweralkoxy, halogen or trifluoromethyl.

The term acyl shall mean a substituent having the formula

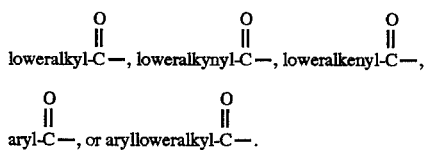

Throughout the specification and the appended claims, a given chemical formula or name shall encompass all stereo, optical, geometrical and tautomeric isomers where such isomers exist.

The compounds of this invention are prepared in the following manner. The substituents $R_1$, $R_2$, $R_3$, X and n shall have the respective meanings given above unless otherwise stated or indicated.

PREPARATION

The starting aminoindoles of formula II can be prepared by methods known in the art, for instance, by utilizing the reduction of nitroindoles with hydrogen and a catalyst. Reference in this regard is made to "Indoles", Part II, edited by W. J. Houlihan, Wiley-Interscience, New York, 1972.

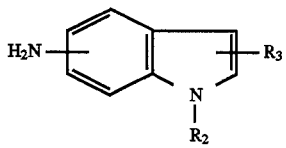

(II)

The starting aminobenzo[b]thiophenes of formula III can be prepared by methods known in the art, for instance as disclosed in Bordwell and Stange, J. Amer. Chem. Soc. 77, 5939 (1955) or Martin-Smith and Gates, J. Amer. Chem. Soc. 78, 5351 (1956).

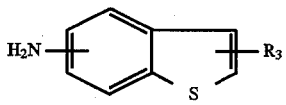

(III)

The starting aminoindazoles of formula IV (a) and (b) can also be prepared by methods known in the art, for instance by the method taught in Prime et al., J. Heterocyclic Chem. 13, 899 (1976).

The indazoles of this invention can be either 1H- or 2H-indazoles as shown below.

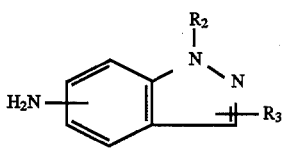

(IV)

1H
(IVa)

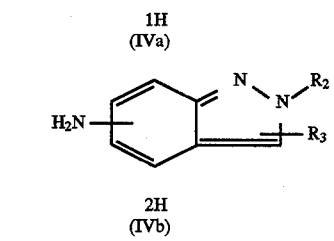

2H
(IVb)

The starting benzisothiazoles of formula V can be prepared by methods known in the art, for instance as disclosed in Adams and Slack, J. Chem. Soc. 3061 (1959).

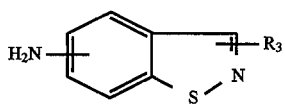

Compound II is allowed to react with a halopyridine hydrochloride of formula VI to afford Compound VII.

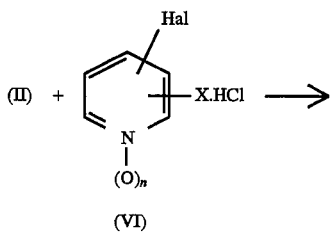

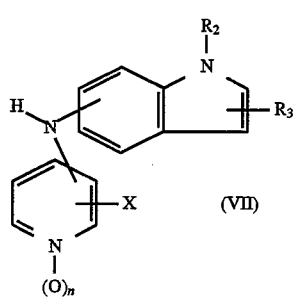

This reaction typically takes place in a suitable solvent such as 1-methyl-2-pyrrolidinone, dimethylformamide or isopropanol at a temperature of between about 20° C. and 200° C. for 1 to 24 hours.

Similarly, compounds III, IV and V are allowed to react with compound VI in substantially the same manner to afford the respective substituted benzo[b]thiophene, indazole and benzisothiazole derivatives.

Compound VII is allowed to react with an alkylating agent of the formula $R_7$ Hal where Hal is chlorine, bromine or iodine and $R_7$ is loweralkyl, loweralkenyl, loweralkynyl or arylloweralkyl or with a diloweralkyl sulfate of the formula $(R_8O)_2SO_2$ where $R_8$ is loweralkyl in a routine manner known in the art to afford compound VIII of the formula

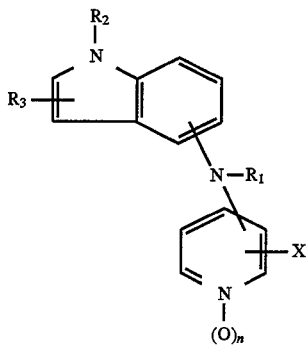

This reaction is conducted in a suitable solvent such as dimethylformamide or tetrahydrofuran in the presence of a suitable base such as sodium or potassium hydride or potassium t-butoxide at a temperature of about 0° to 120° C. for 1 to 24 hours.

Alternatively, Compound VII can react with a loweralkyl chloroformate of the formula

where $R_4$ is loweralkyl to afford a compound of formula IX

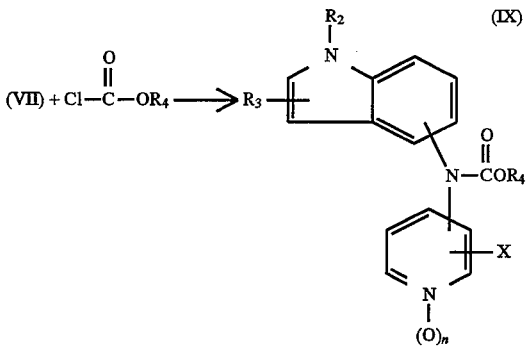

This reaction is typically conducted in a suitable solvent such as a halogenated hydrocarbon, e.g. dichloromethane, or ethereal solvents such as tetrahydrofuran, dimethylformamide or dimethylsulfoxide or aromatic hydrocarbon solvents in the presence of a suitable base such as triethylamine or sodium bicarbonate at a temperature of about −10° to 150° C. for 1 to 24 hours.

To prepare compounds wherein $R_1$ is acyl, compound VII is reacted with an acylating agent of the formula

where Z is halogen and $R'_1$ is loweralkyl, loweralkynyl, loweralkenyl, aryl or arylloweralkyl; or with an acid anhydride of the formula $$(R'_1C)_2O \atop \overset{O}{\|}$$

where $R'_1$ is as previously defined. This reaction is typically conducted in a suitable solvent such as halogenated hydrocarbon solvents, aromatic hydrocarbon solvents or ethereal solvents at a temperature of about −10° to 150° C. for 1 to 24 hours in the presence of a suitable base such as triethylamine or sodium bicarbonate.

Alternatively, to prepare compounds where $R_1$ is loweralkoxycarbonylaminoloweralkylcarbonyl or arylloweralkoxycarbonylaminoloweralkylcarbonyl, compound VII is allowed to react with an N-protected aminoacid such as carbobenzyloxyglycine or N-(tert-butoxycarbonyl) glycine of the formula $$\overset{O}{\underset{\|}{HOCCH_2NHCOR_9}}\overset{O}{\underset{\|}{}} \quad (X)$$

where $R_9$ is arylloweralkyl or loweralkyl in the presence of 1,3-dicyclohexylcarbodiimide to afford compound (XI)

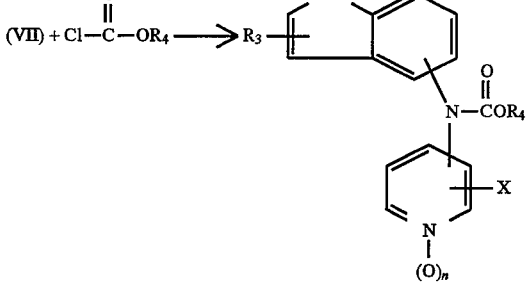

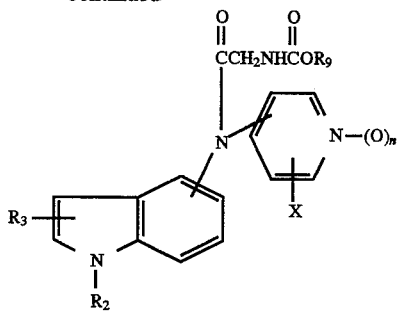

Compound XI is subsequently hydrolyzed in a routine manner know in the art to afford a compound of formula XII

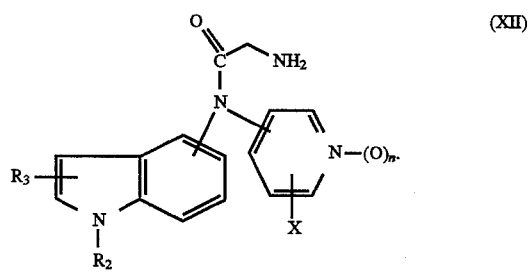

Alternatively, a compound of formula XI where $R_9$ is phenylmethyl is subjected to catalytic hydrogenolysis in a routine manner known in the art to afford a compound of formula XII. This hydrogenation is typically conducted with the aid of a suitable catalyst such as Pd/C, Pt/C or $PtO_2$ and a suitable medium such as ethanol at a temperature of about 20° to 80° C.

The substituted benzo[b]thiophenes, indazoles and benzisothiazoles are prepared in substantially the same manner as outlined above.

The compounds of Formula I of the present invention are useful for the treatment of various memory dysfunctions characterized by a decreased cholinergic function. This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (ACHE) distribution is correlated with central cholinergic innervation. This same innervation is suggested to be weakened in Alzheimer patients. We have determined in vitro inhibition of acetylcholinesterase activity in rat striatum according to the method described below.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in the brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anticholinesterase activity. This is a modification of the method of Ellman et al., Biochem. Pharmacol. 7, 88 (1961).

Procedure

A. Reagents 1. 0.05M Phosphate buffer, pH 7.2
   (a) 6.85 g $NaH_2PO_4 \cdot H_2O$/100 ml distilled $H_2O$
   (b) 13.40 g $Na_2HPO_4 \cdot 7H_2O$/100 ml distilled $H_2O$
   (c) add (a) to (b) until pH reaches 7.2
   (d) Dilute 1:10
2. Substrate in buffer
   (a) 198 mg acetylthiocholine chloride (10 mM)
   (b) bring to 100 ml with 0.05M phosphate buffer, pH 7.2
3. DTNB in buffer
   (a) 19.8 mg 5,5-dithiobisnitrobenzoic acid (DTNB) (0.5 mM)
   (b) bring to 100 ml with 0.05M phosphate buffer, pH 7.2
4. A 2 mM stock solution of the test drug is made up in a suitable solvent and brought to volume with 0.5 mM DTNB (reagent 3). Drugs are serially diluted (1:10) such that the final concentration (in cuvette) is $10^{-4}M$ and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2, using a Potter-Elvehjem homogenizer. A 25 microliter aliquot of the homogenate is added to 1 ml of vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)

Program #6 Kindata:

Source Vis

Wavelength 412 nm

Sipper none

Cuvettes 2 ml cuvettes using auto 6-sampler

Blank 1 for each substrate concentration

Interval time 15 seconds ( 15 or 30 seconds for kinetics)

Total time 5 minutes (5 or 10 minutes for kinetics)

Plot yes

Span autoscale

Slope increasing

Results yes (gives slope)

Factor 1

Reagents are added to the blank and sample cuvettes as follows:

Blank:

0.8 ml Phosphate Buffer/DTNB 0.8 ml Buffer/Substrate

Control:

0.8 ml Phosphate Buffer/DTNB/Enzyme 0.8 ml Phosphate Buffer/Substrate

Drug:

0.8 ml Phosphate Buffer/DTNB/Drug/Enzyme 0.8 ml Phosphate Buffer/Substrate

Blank values are determined for each run to control non-enzymatic hydrolysis of substrate and these values are automatically subtracted by the kindata program available on kinetics soft-pac module. This program also calculates the rate of absorbance change for each cuvette.

For IC$_{50}$ Determinations

Substrate concentration is 10 mM diluted 1:2 in assay yielding final concentration of 5 mM. DTNB concentration is 0.5 mM yielding 0.25 mM final concentration $$\% \text{ Inhibition} = \frac{\text{slope control} - \text{slope drug}}{\text{slope control}} \times 100$$

Results of this assay for some of the compounds of this invention and physostigmine (reference compound) are presented in Table 1.

TABLE 1

| Compound | Inhibitory Concentration (µM) Brain AChE |
|---|---|
| 1-Methyl-5-(propyl-4-pyridinylamino)-1H-indole maleate | 31.85 |
| Physostigmine (reference) | 0.006 |

The compounds of Formula I of the present invention are also useful as modulators of neurotransmitter function such as manifested by the following biochemical assays.

[$^3$H]-Serotonin Uptake in Rat Whole Brain and Hypothalamic Synaptosomes

The compounds of the present invention may also be useful for the treatment of depression and/or obsessive-compulsive disorders by virtue of their ability to inhibit the reuptake of serotonin.

Some researchers have suggested that subjects with serotonergic hypofunction comprise a biochemical subgroup of depressed patients. Others claim that altered serotonergic function determines the change associated with obsessive-compulsive disorder.

This activity is determined in an assay which measures [$^3$H]-serotonin uptake in rat whole brain and hypothalamic synaptosomes. The assay described below is used as a biochemical screen for potential antidepressants which block serotonin (5-hydroxytryptamine, 5HT) uptake.

[$^3$H]-5HT transport has been characterized in the central nervous system tissue and found to be saturable, sodium and temperature-dependent, inhibited by ouabain, metabolic inhibitors, tryptamine analogs and tricyclic antidepressants.

Procedure

A. Animals

Male CR Wistar rats (100–125 g)

B. Reagents

1. Krebs-Henseleit Bicarbonate Buffer, pH 7.4 (KHBB):

Prepare a 1 liter batch containing the following salts.

| | grams/l | mM |
|---|---|---|
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |
| Prior to use add: | | |
| Dextrose | 2 mg/ml | 11.1 |
| Iproniazid phosphate | 0.30 mg/ml | 0.1 |

The batch is aerated for 60 minutes with 95% O$_2$/5% CO$_2$, the pH is checked to insure it is at 7.4±0.1.

2. Add 0.32M sucrose: 21.9 g of sucrose, bring to 200 ml.

3. A 0.1 mM stock solution of serotonin creatinine SO$_4$ is made up in 0.01 N HCl. This is used to dilute the specific activity of the radiolabeled 5HT.

4. 5-[1,2-$^3$H(N)]-Hydroxytryptamine creatinine sulfate (serotonin), specific activity 20–30 Ci/mmol, is used.

The final desired concentration of [$^3$H]-5HT in the assay is 50 nM. The dilution factor is 0.8. The KHBB is made up to contain 62.5 nM of [$^3$H]-5HT.

Add to 100 ml of KHBB.

| A) 56.1 µl of 0.1 mM 5HT = | 56.1 nM |
|---|---|
| B) 0.64 nmol of [$^3$H]-5HT = | 6.4 nM |
| | 62.5 nM |

5. For most assays, a 1 mM stock solution of the test compound is made up in a suitable solvent and serially diluted such that the final concentration in the assay ranges from 2×10$^{-8}$ to 2×10$^{-5}$M. Seven concentrations are used for each assay.

C. Tissue Preparation

Male Wistar rats are decapitated and the brain rapidly removed. Either whole brain minus cerebella or the hypothalamus is weighed and homogenized in 9 volumes of ice-cold 0.32M sucrose using a Potter-Elvejhem homogenizer. The homogenate is centrifuged at 1000 g for 10 minutes at 0°–4° C. The supernatant (S$_1$) is decanted and is used for uptake determination.

D. Assay

800 µl KHBB+[$^3$H]-5HT

20 µl Vehicle or appropriate drug

200 µl Tissue suspension concentration

Tubes are incubated at 37° C. under a 95% O$_2$/5% CO$_2$ atmosphere for 5 minutes. For each assay, 3 tubes are incubated with 20 µl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100 and 50% ethanol, 1:4 v/v). The tubes are vigorously vortexted, decanted into scintillation vials, and counted in 10 ml of Liquiscint scintillation counting cocktail. Active uptake is the difference between cpm at 37° C. and 0° C. The per cent inhibition at each drug concentration is the mean of three determinations. IC$_{50}$ values are derived from log-probit analysis.

[³H]-Norepinephrine Uptake in Rat Whole Brain Synaptosomes

This assay is used as a biochemical screen for compounds that enhance adrenergic mechanisms by blocking norepinephrine uptake.

The neuronal reuptake mechanism for norepinephrine (NE) is the most important physiological means for inactivating NE by removing the transmitter from the synaptic cleft. NE uptake is accomplished by a saturable, stereospecific, high affinity, sodium dependent, active transport system, which has been shown to exist in both peripheral and central nervous system tissue. NE uptake is potently inhibited by cocaine, phenethylamines and tricyclic antidepressants. It is also inhibited by ouabain, metabolic inhibitors and phenoxybenzamine. The inhibition of NE uptake by clinically effective tricyclic antidepressants is an important link in the catecholamine hypothesis of affective disorders and extensive structure activity relationships for NE uptake have been worked out.

There are large regional variations in NE uptake which correlate with the endogenous levels of NE. The hypothalamus shows the highest level of NE and the greatest uptake. Synaptosomal [³H]-NE uptake is a useful marker for the integrity of noreadrenergic neurons, after lesioning experiments, as well as an assay for compounds which potentiate the action of NE by blocking the reuptake mechanism.

Procedure

A. Animals: Male CR Wistar rats (100–125 g).

B. Reagents

1. Krebs-Henseleit Bicarbonate Buffer, pH 7.4 (KHBB)
   Make a 1 liter batch, containing the following salts.

|  | grams/L | mM |
|---|---|---|
| NaCl | 6.92 | 118.4 |
| KCl | 0.35 | 4.7 |
| MgSO₄·7H₂O | 0.29 | 2.2 |
| NaHCO₃ | 2.10 | 24.9 |
| CaCl₂ | 0.14 | 1.3 |
| Prior to use add: |  |  |
| Dextrose | 2 mg/ml | 11.1 |
| Iproniazid phosphate | 0.30 mg/ml | 0.1 |

Aerate for 60 min. with 95% $O_2$/5% $CO_2$, check pH (7.4 ±0.1).

2. 0.32M Sucrose: 21.9 g of sucrose, bring to 200 ml.
3. A 0.1 mM stock solution of L(−)-norepinephrine bitartrate is made up in 0.01 N HCl. This is used to dilute the specific activity of radiolabeled NE.
4. Levo-[Ring-2,5,6-³H]-Norepinephrine (40–50 Ci/mmol) is obtained from New England Nuclear.

The final desired concentration of [³H]-NE in the assay is 50 nM. The 4 dilution factor is 0.8; therefore the KHBB is made up to contain 62.5 nM [³H]-NE.

Add to 100 ml of KHBB:

| A. 59.4 µl of 0.1 mM NE = | 59.4 nM |
|---|---|
| *B. 0.31 nmoles of [³H]-NE = | 3.1 nM |
|  | 62.5 nM |

*Calculate volume added from the specific activity of [³H]-NE.

5. For most assays, a 1 mM stock solution of the test compound is made up in suitable solvent and serially diluted such that the final concentration in the assay ranges from $2 \times 10^{-8}$ to $2 \times 10^{-5}$M. Seven concentrations are used for each assay. Higher or lower concentrations may be used depending on the potency of the test compound.

C. Tissue Preparation

Male Wistar rats are decapitated and brains rapidly removed. Either whole brain minus cerebella or the hypothalamus is weighed and homogenized in 9 volumes of ice-cold 0.32M sucrose using a Potter-Elvejhem homogenizer. Homogenization should be done with 4–5 up and down strokes at medium speeds to minimize synaptosome lysis. The homogenate is centrifuged at 1000 g for 10 minutes at 0°–4° C. The supernatant ($S_1$) is decanted and is used for uptake experiments.

D. Assay

| 800 µl | KHBB containing [³H]-NE |
|---|---|
| 20 µl | Vehicle or appropriate drug concentration |
| 200 µl | Tissue suspension |

Tubes are incubated at 37° C. under a 95% $O_2$/5% $CO_2$ atmosphere for 5 minutes. For each assay, 3 tubes are incubated with 20 µl of vehicle at 0° C. in an ice bath. After incubation all tubes are immediately centrifuged at 4000 g for 10 minutes.

The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The per cent inhibition at each drug concentration is the mean of three determinations. Inhibitory concentration ($IC_{50}$) values are derived from log-probit analysis. (Ref.: Snyder and Coyle, J. Pharmacol. Exp. Ther. 165, 78–86 (1969)).

[³H]-Clonidine Binding: $\alpha_2$-Receptor

Purpose

The purpose of this assay is to assess the interaction of compounds with central $\alpha_2$-receptors. Clonidine acts at both peripheral and central $\alpha_2$-receptors, and functional studies ([³H]-NE release) indicate a presynaptic mechanism for clonidine in either the CNS or periphery. Clonidine binding may be relevant to the activity of certain classes of drugs such as antidepressants and antihypertensive agents that interact with $\alpha_2$-receptors.

Procedure

A. Reagents

1. Tris buffer, pH 7.7
   a.
      57.2 g Tris HCl

11

16.2 Tris Base—bring to 1 liter (0.5M Tris buffer, pH 7.7)

b. Make a 1:10 dilution in distilled $H_2O$ (0.05M Tris buffer, pH 7.7)

2. Tris buffer containing physiological ions
   a. Stock buffer

| | |
|---|---|
| NaCl | 7.014 g |
| KCl | 0.372 g |
| $CaCl_2$ | 0.222 g - bring to 100 ml in 0.5M Tris buffer |
| $MgCl_2$ | 0.204 g | b. Dilute 1:10 in distilled $H_2O$. This yields 0.05 M Tris HCl, pH 7.7; containing NaCl (120 mM), KCl (5 mM), $CaCl_2$ (2 mM) and $MgCl_2$ (1 mM)

3. [4-$^3$H]-Clonidine hydrochloride (20–30 Ci/mmol) is obtained from New England Nuclear. For $IC_{50}$ determinations: [$^3$H]-Clonidine is made up to a concentration of 120 nM and 50 gl added to each tube (yields a final concentration of 3 nM in the 2 ml volume assay).

4. Clonidine-HCl is obtained from Boehringer Ingelheim. A stock solution of 0.1 mM clonidine is made up to determine nonspecific binding. This yields a final concentration of 1 µM in the assay (20 µl to 2 ml).

5. Test compounds. For most assays, a 1 mM stock solution is made up in a suitable solvent and serially diluted, such that the final concentration in the assay ranges from $10^{-5}$ to $10^{-8}$ M. Seven concentrations are used for each assay and higher or lower concentrations may be used, depending on the potency of the drug.

B. Tissue Preparation

Male Wistar rats are sacrificed by decapitation and the cortical tissue rapidly dissected. The tissue is homogenized in 50 volumes of 0.05M Tris buffer, pH 7.7 (buffer 1b) with the Brinkman Polytron, then centrifuged at 40,000 g for 15 minutes. The supernatant is discarded and the pellet rehomogenized in the original volume of 0.05M Tris buffer, pH 7.7 and recentrifuged as before. The supernatant is discarded and the final pellet rehomogenized in 50 volumes of Buffer 2b. This tissue suspension is then stored on ice. The final tissue concentration is 10 mg/ml. Specific binding is 1% of the total added ligand and 80% of total bound ligand.

C. Assay

| | |
|---|---|
| 100 µl | 0.5M Tris-physiological salts, pH 7.7 (buffer 2a) |
| 830 µl | $H_2O$ |
| 20 µl | Vehicle (for total binding) or 0.1 mM clonidine (for nonspecific binding) or appropriate drug concentration |
| 50 µl | [$^3$H]-clonidine stock |
| 1000 µl | Tissue suspension |

Tissue homogenates are incubated for 20 minutes at 25° C. with 3 nM [$^3$H]-clonidine and varying drag concentrations, then immediately filtered under reduced pressure on Whatman GF/B filters. The filters are washed with three five ml volumes of ice-cold 0.05M Tris buffer, pH 7.7, then transferred to scintillation vials. Ten ml of liquiscint counting solution is added to each sample which is then counted by liquid scintillation spectroscopy. Specific clonidine binding is defined as the difference between total bound and that performed in the presence of unlabeled clonidine. The percent inhibition at each drug concentration is the mean of triplicate determinations. $IC_{50}$ values are calculated using log-probit analysis. (Ref.: U. Pritchard et al., Mol. Pharmacol. 13, 454–473 (1977)).

12

Results of the three assay methods described above are presented in Table 2 for representative compounds of this invention.

TABLE 2

| Compound | 5-HT Uptake $IC_{50}$(µM) | NE Uptake $IC_{50}$ (µM) | [$^3$H]-Clonidine Binding $IC_{50}$ (µM) |
|---|---|---|---|
| 1-Methyl-5-(4-pyridinyl-amino)-1H-indole | | | 0.012 |
| 1-Methyl-5-(propyl-4-pyridinylamino)-1H-indole maleate | 0.76 | 0.034 | 0.33 |
| Amitriptyline (ref.) | | 7.7 | 3.9 |
| Notriptyline (ref.) | | 4.0 | |
| Chloripramine (ref.) | 0.15 | | |
| Fluoxetine (ref.) | 0.25 | | |
| Mianserin (ref.) | | | 0.10 |

Compounds of the present invention show efficacy as modulators of neurotransmitter function when administered to a subject requiting such treatment as an effective, oral, parenteral or intravenous dose of from about 0.01 to 100 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

The compounds of the present invention are also useful as topical antiinflammatory agents for the treatment of various dermatoses which may include, for example, exogenous dermatitides (e.g., sunburn, photoallergic dermatitis, urticaria, contact dermatitis, allergic dermatitis), endogenous dermatitides (e.g., atopic dermatitis, seborrheic dermatitis, nummular dermatitis), dermatitides of unknown etiology (e.g., generalized exfoliative dermatitis), and other cutaneous disorders with an inflammatory component (e.g., psoriasis).

The dermatological activity of the compounds was ascertained according to the following method.

TPA-Induced Ear Edema (TPAEE)

The purpose of this assay was to determine the ability of a topically applied compound to prevent ear edema induced by topical application of TPA (phorbol 12-myristate acetate). Female Swiss Webster mice topically received TPA (10 µg/ear) on the right ear and vehicle on the left ear. The test compound (10 µg/ear) was applied to both ears. After about 5 hours, the animals are sacrificed and a 4 mm diameter plug is taken from each ear and weighed. The difference between the tight and left ear plug weights for each animal was determined. The antiinflammatory activity of the test compound is expressed as the mean percent change in ear plug weight of the treated animals compared to the mean percent change in the plug weight of the control animals. (Young, J. M. et al., J. Invest. Dermatol., 80 (1983), pp. 48–52.)

TABLE 3

| Compound | Edema Reduction (10 µg/ear) |
|---|---|
| 1-Methyl-5-(4-pyridinylamino)-1H-indole | −67% |
| Indomethacin (reference) | −86% at 1 mg/ear |

Inflammation reduction is achieved when the compounds of the invention are administered topically, including opthalmic administration, to a subject requiring such treatment as an effective topical dose of from 0.01 to 100 mg/kg of body weight per day. A preferred effective amount is about 10 to 50 mg/kg of body weight per day. It is to be understood however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective quantities of the compounds of the present invention may be administered to a subject by any one of various methods, for example, orally as in capsules or tablets, parenterally in the form of sterile solutions or suspensions, topically as in ointments, solutions or salves, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel™, corn starch and the like; a lubricant such as magnesium stearate or Sterotex®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For the purpose of topical administration, the active compounds of the invention may be incorporated into a solution, suspension, ointment, cream, gel, aerosol or salve. These preparations should contain at least 0.1% of active compound but may be varied to be between 0.05 and about 20% of the weight thereof. The amount of active compound in such compositions is such that a suitable dosage will be obtained. Preferred topically administered preparations should contain between 0.1 and 10% of active compound.

The topical compositions may also include the following components: water, fixed oils, polyethylene glycols, glycerol, petroleum stearic acid, beeswax, other synthetic solvents or mixtures thereof; antibacterial agents such as benzyl alcohol or methyl paraben; antioxidants such as α-tocopherol acetate; chelating agents such as ethylenediaminetetraacetic acid (EDTA); buffers such as acetates, citrates or phosphates; emulsifying agent such as polyoxyethylene monooleate and coloring materials and adjuvants such as ferric oxide or talc. The topical preparation can be enclosed in tubes, bottles or jars made of metal, glass or plastic.

Examples of the compounds of this invention include:
1-Methyl-5-(4-pyridinylamino)-1H-indole;
1-Methyl-5-(propyl-4-pyridinylamino)-1H-indole;
5-4-Pyridinylamino)-1H-indole;
5-(Propyl-4-pyridinylamino)-1H-indole;
N-(1-Methyl-1H-indol-5-yl)-N-(4-pyridinyl)-2-aminoacetamide;
5-(Propyl-4-pyridinylamino)-1H-indazole;
5-(4-Pyridinylamino)benzo[b]thiophene;
5-(Propyl-4-pyridinylamino)benzo[b]thiophene;
N-(Benzo[b]thiophen-5-yl)-N-(4-pyridinyl)-2-aminoacetamide;
5-(4-Pyridinylamino)-1,2-benzisothiazole;
5-(Propyl-4-pyridinylamino)-1,2-benzisothiazole;
6-(4-Pyridinylamino)-1H-indole;
2-Methyl-5-(4-pyridinylamino)-2H-indazole;
6-(4-Pyridinylamino)benzo[b]thiophene;
1-Methyl-5-(4-pyridinylamino)-1H-indazole;
7-(4-Pyridinylamino)benzo[b]thiophene;
5-(3-Pyridinylamino)-1H-indole;
5-(3-Pyridinylamino)benzo[b]thiophene;
1-Methyl-5-(4-pyridinylamino)-1H-indole-$N^5$-oxide;
1-Methyl-5-(propyl-4-pyridinylamino)-1H-indole-$N^5$oxide;
5-(Methyl-4-pyridinylamino)benzo[b]thiophene- $N^5$-oxide;
5-(4-Pyridinylamino)-1,2-benzisothiazole-$N^5$-oxide; and
6-(3-Pyridinylamino)benzo[b]thiophene-$N^6$-oxide.

The following examples are for illustrative purposes and are not to be construed as limiting the invention disclosed herein. All temperatures are given in degrees centigrade (°C.) unless indicated otherwise.

EXAMPLE 1

1-Methyl-5-(4-pyridinylamino)-1H-indole

4-Chloropyridine hydrochloride (8 g) was added to a solution of 5-amino-1-methylindole (7 g) in 75 ml 1-methyl-2-pyrrolidinone preheated to 100° C. The addition of 4-chloropyridine hydrochloride (4 g) after one hour caused no further reaction as determined by TLC. After two hours the reaction mixture was cooled, stirred with water, basified with sodium carbonate and extracted with ethyl acetate. The dried (anhydrous magnesium sulfate) organic layer was filtered and evaporated to 12.7 g of an oil. The oil was eluted through silica with 10% methanol in dichloromethane via flash column chromatography to give the product which was triturated with ether to yield 5.7 g of a solid, m.p. 202°–203° C. Recrystallization from acetonitrile yielded 5 g of product as crystals, mp 209°–211° C.

Analysis:

| | | | |
|---|---|---|---|
| Calculated for $C_{14}H_{13}N_3$: | 75.31% C | 5.87% H | 18.82% N |
| Found: | 75.13% C | 6.08% H | 18.76% N |

EXAMPLE 2

1-Methyl-5-(Propyl-4-pyridinylamino)-1H-indole Maleate

Potassium-tert-butoxide (2 g) was added portionwise to an ice-cooled solution of 1-methyl-5-(4-pyridinylamino)-1H-indole (3 g) in 50 ml tetrahydrofuran. After ten minutes a solution of 1-bromopropane (2 g) in 10 ml tetrahydrofuran was added dropwise. The reaction mixture slowly warmed to ambient temperature, and then was stirred with water and extracted with ethyl acetate. The organic layer was washed with water and saturated sodium chloride, and then dried (anhydrous magnesium sulfate), filtered and evaporated to 3.5 g of an oil. The oil was eluted through silica with 5% methanol in dichloromethane via flash column chromatography to yield 3.1 g of the product as an oil. This was converted to the maleate salt in methanol-ether to yield 3.5 g of product as crystals, mp 136–138° C.

Analysis:

| | | | |
|---|---|---|---|
| Calculated for $C_{21}H_{23}N_3O_4$: | 66.12% C | 6.08% H | 11.02% N |
| Found: | 66.06% C | 5.99% H | 10.95% N |

EXAMPLE 3

N-(1-Methyl-1H-indol-5-yl)-N-(4-pyridinyl)-2-(Carbamic Acid, Phenylmethyl Ester)Acetamide Hydrochloride 1,3-Dicyclohexylcarbodiimide (6 g) was added to a solution of 1-methyl-5-(4-pyridinylamino)-1H-indole (6.2 g) and carbobenzyloxyglycine (5.8 g) in 200 ml of dichloromethane (DCM). After stirring one hour at ambient temperature the reaction mixture was filtered to remove the 1,3-dicyclohexylurea by-product and evaporated to 12 g of a solid. Elution through silica with 50% ethyl acetate in DCM via flash column chromatography yielded 9 g of a solid. A 1.5 g portion was converted to the hydrochloride salt in 20% methanol in ether to yield 1.35 g of crystals, mp 166°–168° (dec.). Recrystallization from 20% methanol in ether yielded 1.1 g of crystals, mp 170°–172° C. (dec.).

Analysis:

| | | | |
|---|---|---|---|
| Calculated for $C_{24}H_{23}ClN_4O_3$: | 63.92% C | 5.14% H | 12.43% N |
| Found: | 63.58% C | 5.36% H | 12.28% N |

EXAMPLE 4

N-(1-Methyl-1H-indol-5-yl)-N-(4-pyridinyl) Carbamic Acid Methyl Ester

A solution of methyl chloroformate (1.3 g) in 5 ml DCM was added to a solution of 1-methyl-5-(4-pyridinylamino)-1H-indole (2.5 g) in 120 ml DCM and 6 ml triethylamine (4.4 g). After stirring one hour at ambient temperature the reaction mixture was washed with water and saturated sodium chloride, dried (anhydrous magnesium sulfate), filtered and evaporated to 4 g of a solid. Elution through silica with 50% ethyl acetate in dichloromethane via flash column chromatography yielded 3.1 g of a solid. Recrystallization from methanol yielded 2.4 g of crystals, mp 157°–159° C.

Analysis:

| | | | |
|---|---|---|---|
| Calculated for $C_{16}H_{15}N_3O_2$: | 68.31% C | 5.37% H | 14.94% N |
| Found: | 68.36% C | 5.38% H | 14.98% N |

EXAMPLE 5

5-(4-Pyridinylamino)-1H-indazole

4-Chloropyridine hydrochloride (15 g) was added as a powder to a solution of 5-aminoindazole (10 g) in 220 ml 1-methyl-2-pyrrolidinone, preheated to 75°–80°. After three hours the mixture was cooled, stirred with water, basified with sodium carbonate and extracted with ethyl acetate. The organic extract was washed with water and saturated NaCl then was dried (anhydrous magnesium sulfate), filtered and evaporated to an oil. Elution through silica with 15% methanol in DCM via HPLC yielded 6.1 g of a solid. Trituration with acetonitrile yielded 5.2 g of a solid, mp 184°–186° C. This was further purified by eluting through silica with 10% methanol in ethyl acetate via flash column chromatography to yield 4.4 g of a solid. Recrystallization from acetonitrile yielded 3.3 g of 5-(4-pyridinylamino)-1H-indazole, as crystals, mp 189°–190° C.

Analysis:

| | | | |
|---|---|---|---|
| Calculated for $C_{12}H_{10}N_4$: | 68.56% C | 4.79% H | 26.65% N |
| Found: | 68.26% C | 4.81% H | 26.57% N |

We claim:

1. A method of treating a patient in need of relief from a memory dysfunction which comprises administering to said patient an effective amount of compound of the formula

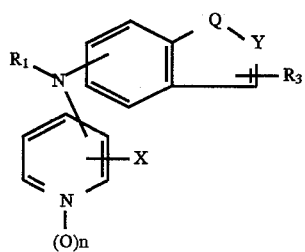

wherein

Q is S, N or NR$_2$;

Y is CH, N or NR$_2$;

R$_1$ is hydrogen, loweralkyl, loweralkynyl, loweralkenyl, arylloweralkyl, loweralkoxycarbonylaminoloweralkylcarbonyl, arylloweralkoxycarbonylaminoloweralkylcarbonyl, aminoloweralkylcarbonyl, loweralkoxycarbonyl or acyl;

R$_2$ is hydrogen or loweralkyl;

R$_3$ is hydrogen or loweralkyl;

X is hydrogen, loweralkyl or halogen; and n is 0 or 1; or a pharmaceutically acceptable acid addition salt thereof.

* * * * *

UNITED STATES PATENT AND TRADEMARK OFFICE
CERTIFICATE OF CORRECTION

PATENT NO.   :  5,631,270

DATED        :  May 20, 1997

INVENTOR(s)  :  Richard C. Effland, et al.

It is certified that error appears in the above-identified patent and that said Letters Patent is hereby corrected as shown below:

At column 5, line 47, the patent reads "(ACHE)" and should read --(AChE) .

At column 8, line 58, the patent reads "supermatant" and should read --supernatant--.

At column 9, line 65, the patent reads "The 4 dilution" and should read --The dilution-- .

At column 11, line 20, the patent reads "50 gl" and should read --50 µl-- .

At column 11, line 55, the patent reads "drag" and should read --drug-- .

At column 12, line 22, the patent reads "requiting" and should read --requiring-- .

At column 12, line 52, the patent reads "tight" and should read --right-- .

Signed and Sealed this

Sixth Day of April, 1999

Attest:

Q. TODD DICKINSON

*Attesting Officer*    *Acting Commissioner of Patents and Trademarks*